(12) United States Patent
Grushin et al.

(10) Patent No.: US 6,875,523 B2
(45) Date of Patent: Apr. 5, 2005

(54) PHOTOACTIVE LANTHANIDE COMPLEXES WITH PHOSPHINE OXIDES, PHOSPHINE OXIDE-SULFIDES, PYRIDINE N-OXIDES, AND PHOSPHINE OXIDE-PYRIDINE N-OXIDES, AND DEVICES MADE WITH SUCH COMPLEXES

(75) Inventors: Vladimir Grushin, Hockessin, DE (US); Norman Herron, Newark, DE (US); Viacheslav Alexandrovich Petrov, Hockessin, DE (US); Nora Sabina Radu, Landenberg, PA (US); Ying Wang, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 185 days.

(21) Appl. No.: 10/185,484

(22) Filed: Jun. 27, 2002

(65) Prior Publication Data

US 2003/0144487 A1 Jul. 31, 2003

Related U.S. Application Data

(60) Provisional application No. 60/303,283, filed on Jul. 5, 2001.

(51) Int. Cl.$^7$ .......................... H05B 33/14; C09K 11/06; C07F 9/53
(52) U.S. Cl. ........................ 428/690; 428/917; 313/504; 313/506; 257/40; 252/301.16; 546/6; 546/21; 556/18; 556/21
(58) Field of Search .................... 252/301.16; 428/690, 428/917; 313/504, 506; 257/40; 546/2, 6, 21, 22; 556/18, 19, 20, 21

(56) References Cited

U.S. PATENT DOCUMENTS

| 5,128,587 A | 7/1992 | Skotheim et al. ........... 313/504 |
| 5,756,224 A | 5/1998 | Börner et al. ............... 428/690 |

FOREIGN PATENT DOCUMENTS

| EP | 0556005 B1 | 4/1996 |
| EP | 0744451 B1 | 7/1999 |
| JP | 2505244 B2 | 6/1996 |
| JP | 2002-124383 A | * 4/2002 |
| JP | 2003-81986 A | * 3/2003 |
| WO | WO 98/58037 A1 | 12/1998 |

OTHER PUBLICATIONS

An 1969:71525 HCAPLUS (for Carey et al., "Synergic solvent extraction ... with various alkylphosphine oxides", Journal of Inorganic and Nuclear Chemistry (1969), 31(2), 553–50).*
An 1993:461623 HCAPLUS (for Kalinovskaya et al., "Europium ... phosphorus–containing neutral ligands", Zhurnal Neorganicheskoi Khimii (1993), 38(2), 288–90).*
An 2002:313481 (for JP 2002–124383 A, Apr. 2002).*
An 2003:214732 HCAPLUS (for JP 2003–81986 A, Mar. 2003).*
Gao, X. C., et al., Electroluminescence of a novel terbium complex, Applied Physics Letters, May 4, 1996, 2217–2219, vol. 72, No. 18, American Institute of Physics.

* cited by examiner

Primary Examiner—Marie Yamnitzky

(57) ABSTRACT

The present invention is generally directed to luminescent lanthanide compounds with phosphine oxide, phosphine oxide-sulfide, pyridine N-oxide, and phosphine oxide-pyridine N-oxide ligands. It also relates to electronic devices in which the active layer includes a lanthanide complex.

12 Claims, 3 Drawing Sheets

(VIII)

(XVII)

PHOTOACTIVE LANTHANIDE COMPLEXES WITH PHOSPHINE OXIDES, PHOSPHINE OXIDE-SULFIDES, PYRIDINE N-OXIDES, AND PHOSPHINE OXIDE-PYRIDINE N-OXIDES, AND DEVICES MADE WITH SUCH COMPLEXES

RELATED APPLICATIONS

This application is a non-provisional of U.S. Provisional Application No. 60/303,283 filed Jul. 5, 2001, the content of which is herein incorporated by reference.

BACKGROUND OF THE INVENTION

1. Field of the Invention

This invention relates to photoactive complexes of lanthanide metals with phosphine oxide, phosphine oxide-sulfides, pyridine N-oxide, or phosphine oxide-pyridine N-oxide ligands. It also relates to electronic devices in which the active layer includes a photoactive lanthanide complex.

2. Description of the Related Art

Photoactive compounds are of interest in a variety of applications, including analytical, bio-analytical and electronic uses. Extensive studies have been made of compounds of the lanthanide metals because of their characteristic sharp emission spectra with very narrow peak-widths. Analytical uses of luminescent complexes of lanthanide metals have been disclosed by, for example, Bell et al. in EP 556 005 and EP 744 451.

Organic electronic devices such as devices that emit light, such as light-emitting diodes that make up displays, are present in many different kinds of electronic equipment. In all such devices, a photoactive layer is sandwiched between two electrical contact layers. At least one of the electrical contact layers is light-transmitting so that light can pass through the electrical contact layer. The photoactive layer emits light through the light-transmitting electrical contact layer upon application of electricity across the electrical contact layers.

It is well known to use organic electroluminescent compounds as the active component in light-emitting diodes. Electronic devices using luminescent organometallic complexes of lanthanide metals have also been disclosed. In most devices the lanthanide centers are bound to diimine ligands, such as Skotheim et al., U.S. Pat. No. 5,128,587, and Borner et al., U.S. Pat. No. 5,756,224. Heeger et al. have reported devices using europium complexes blended with semiconducting conjugated polymers (*Adv. Mater.* 1999, 11, 1349). Devices containing lanthanide centers bound to phosphineoxide ligands have been disclosed in, for example, Kathirgamanathan et al. WO98/58037, Wenlian et al. *Journal of the SID* 1998, 6, 133, and Gao et al. *Appl. Phys. Lett.* 1998, 72, 2217.

There is a continuing need for improved photoactive lanthanide compounds. Futhermore, the synthesis and luminescent properties of lanthanide complexes bound to phosphine oxide, phosphine oxide-sulfide, N-oxide or phosphine oxide-pyridine N-oxide ligands have remained largely unexplored.

SUMMARY OF THE INVENTION

The present invention is directed to a photoactive compound comprising at least one lanthanide metal compound. The lanthanide metal compound includes at least one lanthanide metal which is complexed to at least one ligand selected from monophosphine oxides having Formula I shown in FIG. 1; bisphosphine dioxides having Formula II, shown in FIG. 1, where in Formula II, x is 2 and y is 1; trisphosphine trioxide having Formula II, shown in FIG. 1, where in Formula II, x is 1 and y is 2; bis-phosphine oxide-sulfides having Formula III, shown in FIG. 1; pyridine N-oxides having Formula IV, Formula V or Formula VI, shown in FIG. 2; phosphine oxide-pyridine N-oxides having Formula VII, shown in FIG. 3; and combinations thereof, where:

in each of Formulae I, II and III:
Q is the same or different at each occurrence and is selected from $C_6H_nF_{5-n}$, and $C_m(H+F)_{2m+1}$,
m is an integer from 1 to 12, and
n is 0 or an integer from 1 to 5, in Formula I:
Z is selected from Q and pyridyl, with the provision that when Z is Q, there is at least one F substituent on at least one Q group, in each of Formulae II and III:
LG is the same or different at each occurrence and is a linking group selected from $C_m(H+F)_{2m}$, arylene, cyclic heteroalkylene, heteroarylene, alkyleneheteroarylene, ferrocenediyl, and o-carboranediyl, in Formula II:
r is the same or different at each occurrence and is 0 or 1,
x is 1 or 2, and
y is 1 or 2, with the provision that x+y=3, in each of Formulae IV through VII:
Y is the same or different at each occurrence and is selected from —CN, —OR$^1$, —OH, —C(O)OR$^1$, —R$_f$, aryl, X, —NO$_2$, and —SO$_2$R$^1$,
R$^1$ is $C_sH_{2s+1}$,
R$_f$ is $C_sF_{2s+1}$
X is F, Cl, Br, or I,
s is an integer from 1 to 6, in Formula IV:
α is 0 or an integer from 1 to 5, in Formulae V through VII:
β is 0 or an integer from 1 to 4, in Formula V:
δ is 0 or an integer from 1 to 3, and in Formula VII:
m is 0 or an integer from 1–12.

In another embodiment, the present invention is directed to an organic electronic device having at least one photoactive layer comprising the above lanthanide compound, or combinations of the above lanthanide compounds.

As used herein, the term "phosphine oxide ligand" is intended to mean a ligand having one or more phosphine oxide groups, hereinafter shown as "P(O)". The term "bis-phosphine oxide-sulfide ligand" is intended to mean a ligand having one phosphine oxide group and one phosphine sulfide group, where the phosphine sulfide group is hereinafter shown as "P(S)". The term "pyridine N-oxide ligand" is intended to mean a ligand having a substituted or unsubstituted pyridine N-oxide fragment. The term "phosphine oxide-pyridine N-oxide" is intended to mean a ligand having one phosphine oxide group and one pyridine N-oxide fragment.

As used herein, the term "compound" is intended to mean an electrically uncharged substance made up of molecules that further consist of atoms, wherein the atoms cannot be separated by physical means. The term "ligand" is intended to mean a molecule, ion, or atom that is attached to the coordination sphere of a metallic ion or an atom. The term "complex", when used as a noun, is intended to mean a compound having at least one metallic ion and at least one ligand. The term "group" is intended to mean a part of a compound, such as a substituent in an organic compound or a ligand in a complex. The term "β-dicarbonyl" is intended to mean a neutral compound in which two carbonyl groups are present, separated by a CHR group. The term "β-enolate" is intended to mean the anionic form of the β-dicarbonyl in which the H from the CHR group between the two keto groups has been abstracted. The term "charge transport material" is intended to mean material that can receive a charge from an electrode and move it through the thickness of the material with relatively high efficiency and low loss. The phrase "adjacent to," when used to refer to layers in a device, does not necessarily mean that one layer is immediately next to another layer. On the other hand, the phrase "adjacent R groups", is used to refer to R groups that are next to each other in a chemical formula (i.e., R groups that are on atoms joined by a bond). The term "photoactive" refers to any material that exhibits electroluminescence and/or photosensitivity. In addition, the IUPAC numbering system is used throughout, where the groups from the Periodic Table are numbered from left to right as 1–18 (CRC Handbook of Chemistry and Physics, $81^{st}$ Edition, 2000).

DETAILED DESCRIPTION OF THE PREFERRED EMBODIMENTS

In the lanthanide compounds of the invention, the lanthanide metals are in the +3 oxidation state, and are hepta-coordinate or octacoordinate. One or more of the coordination sites are occupied by at least one ligand having one of Formulae I through VII. More than one of these ligands, and more than one type of ligand may be coordinated to the metal. The remaining coordination sites are occupied by additional ligands, such as halides; β-enolates; anions of acids, such as acetic acid, benzoic acid, picolinic acid, and dipicolinic acid; and nitrogen-containing ligands, such as arylamines, bipyridine, terpyridine, phenanthroline and tetramethylenediamine. When the lanthanide compound is applied as a layer by vapor deposition techniques, the ligands are generally chosen so that the final compound is neutral in charge. It is preferred that the additional ligands are β-enolates. More preferred lanthanide compounds are described by one of Formulae IX through XV below:

| | |
|---|---|
| Ln(β-enolate)$_3$(monophosphine oxide)$_1$ | (IX-A) |
| Ln(β-enolate)$_3$(monophosphine oxide)$_2$ | (IX-B) |
| [Ln(β-enolate)$_3$]$_1$(bisphosphine dioxide)$_1$ | (X-A) |
| [Ln(β-enolate)$_3$]$_2$(bisphosphine dioxide)$_1$ | (X-B) |
| [Ln(β-enolate)$_3$]$_1$(trisphosphine trioxide)$_1$ | (XI-A) |
| [Ln(β-enolate)$_3$]$_2$(trisphosphine trioxide)$_1$ | (XI-B) |
| [Ln(β-enolate)$_3$]$_3$(trisphosphine trioxide)$_1$ | (XI-C) |
| Ln(β-enolate)$_3$(bisphosphine oxide-sulfide)$_1$ | (XII-A) |
| Ln(β-enolate)$_3$(bisphosphine oxide-sulfide)$_2$ | (XII-B) |
| Ln$_2$(β-enolate)$_6$(pyridine-N-oxide)$_3$ | (XIII) |
| Ln(β-enolate)$_3$(phosphine oxide-pyridine N-oxide)$_1$ | (XIV) |
| Ln$_2$(β-enolate)$_6$(bisphosphine monoxide)$_2$MX$_2$ | (XV) |

Figure 1:
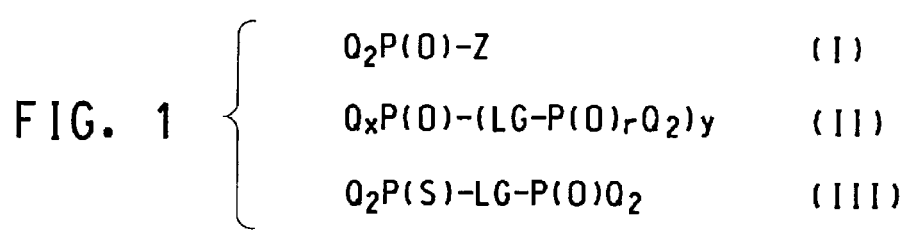
FIG. 1 shows Formula I and Formula II for phosphine oxide ligands, and Formula III for bis-phosphine oxide-sulfide ligands, useful in the invention.
Figure 2:
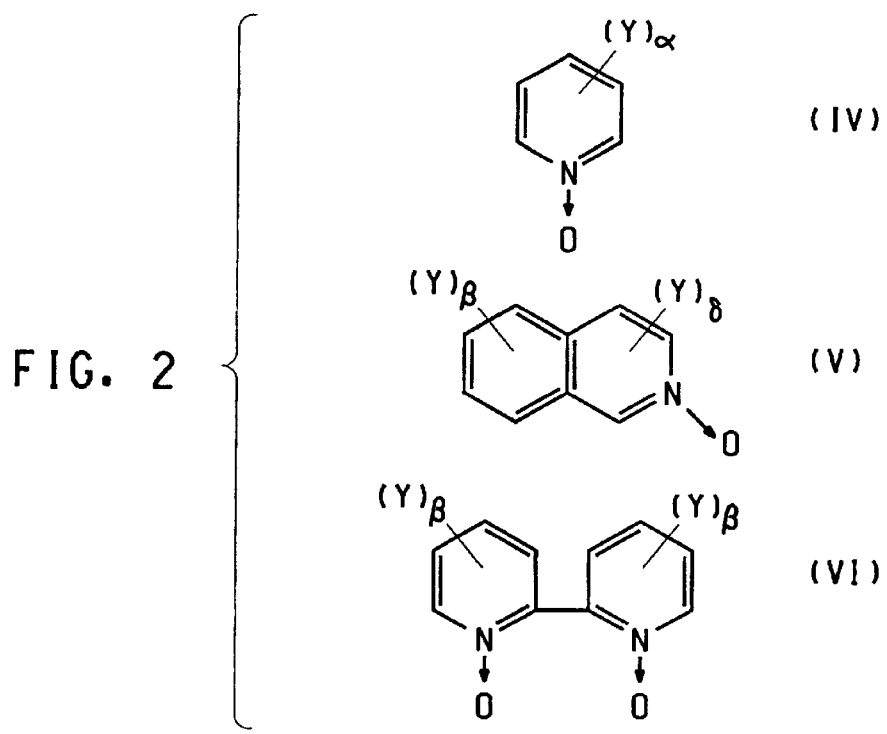
FIG. 2 shows Formulae IV through VI for pyridine N-oxide ligands useful in the invention.
Figure 3:
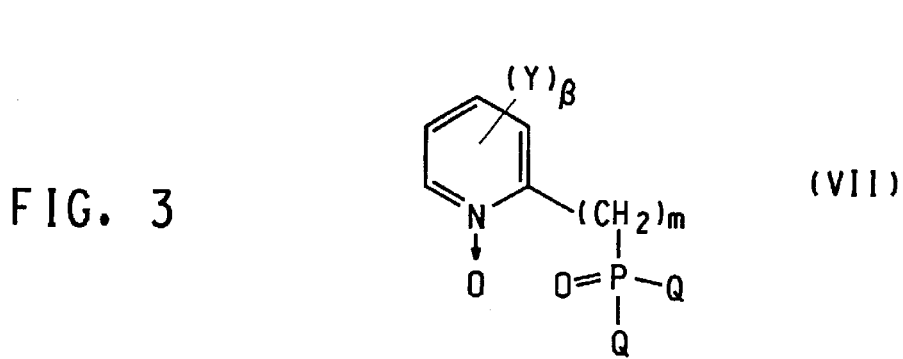
FIG. 3 shows Formula VII for phosphine oxide-pyridine N-oxide ligands useful in the invention.

Where:
in Formulae (IX-A) and (IX-B):
monophosphine oxide has Formula I shown in FIG. 1;
in Formulae (X-A) and (X-B):
bisphosphine dioxide has Formula II, shown in FIG. 1;
where in Formula II, x is 2, y is 1, and r is 1;
in Formulae (XI-A), (XI-B) and (XI-C):
trisphosphine trioxide has Formula II, shown in FIG. 1;
where in Formula II, x is 1, y is 2, and r is 1;
in Formulae (XII-A) and (XI-B):
bis-phosphine oxide-sulfide has Formula III, shown in FIG. 1;
in Formula (XIII):
pyridine N-oxide has Formula IV, Formula V or Formula VI, shown in FIG. 2;
in Formula (XIV):
phosphine oxide-pyridine N-oxide has Formula VII, shown in FIG. 3;
in Formula XV:
bisphosphine monoxide has Formula II, shown in FIG. 1;
where in Formula II, x is 2, y is 1, and r is 0;
M is a transition metal;
X is a monoanionic ligand When ligands having more than one phosphine oxide have long linking groups, it is possible to coordinate more than one lanthanide metal to a single ligand, resulting in compounds having Formula (X-A), (X-B), (XI-A) of (XI-B) with 2 or 3 Ln(β-enolate)$_3$ units. In some cases, oligomeric or polymeric structures can be formed with alternating Ln(β-enolate)$_3$ units and multi(phosphine oxide) ligands.

It is also possible to form complexes having Formula (XV) with a second metal. Preferably the metal M is from Groups 9–11 in the Periodic Table; most preferably Pt. X is an anionic ligand, such as Br⁻, Cl⁻, I-, and CN⁻. It is preferred that X is chloride.

The preferred lanthanide metals are Eu, Tb, and Tm. The preferred lanthanide complexes are neutral and non-ionic, and can be sublimed intact.

Phosphine Oxide Ligands

The phosphine oxide ligands can be monophosphine oxides, bis-phosphine dioxides, or tris-phosphine trioxides, and may include additional phosphine groups, as in Formula II, when r is 0.

The phosphine oxide ligands having Formula I, shown in FIG. 1, have a single phosphine oxide group and no additional phosphine groups. It is preferred that in ligands having this formula at least one of the Q groups has at least one fluorine. More preferably, at least one Q group is —$C_6F_5$; and still more preferably, all the Q groups are —$C_6F_5$.

Examples of suitable monophosphine oxide ligands having Formula I include, but are not limited to those listed in Table (i) below. The abbreviation for the monophosphine oxide is given in brackets.

TABLE (i)

| tris(pentafluorophenyl)phosphine oxide | [$F_5$tpO] |
| 2-(diphenylphosphinoyl)-pyridine | [dpOpy] |

The phosphine oxide ligands having Formula II, shown in FIG. 1, have a phosphine oxide group and at least one additional phosphorus-containing group, which can be a phosphine or a phosphine oxide. The phosphorus atoms are joined together by a linking group. The linking group can be a simple hydrocarbon chain or cyclic group, optionally substituted with fluorine atoms or including heteroatoms in place of carbons. The linking group can also be a more complex group, such as a ferrocene or o-carborane group. When ferrocene is the linking group, one phosphorus atom is attached to each cyclopentadiene ring. When o-carborane is the linking group, a phosphorus atom is attached to each of the two carbon atoms.

Examples of suitable monophosphine oxide ligands having Formula II include, but are not limited to those listed in Table (ii) below. The abbreviation for the monophosphine oxide is given in brackets.

TABLE (ii)

| (diphenylphosphinomethyl)diphenylphosphine oxide | [dppmO] |
| (2-diphenylphosphinoethyl)diphenylphosphine oxide | [dppeO] |
| (3-diphenylphosphinopropyl)diphenylphosphine oxide | [dpppO] |
| (4-diphenylphosphinobutyl)diphenylphosphine oxide | [dppbO] |
| bis(diphenylphosphinomethyl)phenylphosphine oxide | [bisdppmO] |
| bis(2-diphenylphosphinoethyl)phenylphosphine oxide | [bisdppeO] |

Examples of suitable bis-phosphine dioxide and tris-phosphine trioxide ligands having Formula II include, but are not limited to those listed in Table (iii) below. The abbreviation for the ligand is given in brackets.

TABLE (iii)

| bis(diphenylphosphino)methane dioxide | [dppmO$_2$] |
| 1,2-bis(diphenylphosphino)ethane dioxide | [dppeO$_2$] |
| 1,3-bis(diphenylphosphino)propane dioxide | [dpppO$_2$] |
| 1,4-bis(diphenylphosphino)butane dioxide | [dppbO$_2$] |
| 1,1'-bis(diphenylphosphino)ferrocene dioxide | [dppfcO$_2$] |
| 1,2-bis(diphenylphosphoryl)-o-carborane | [dppcbO$_2$], |
| 1,2-bis(di(pentafluorophenyl)phosphino)ethane dioxide | [($F_5$dppeO$_2$] |
| bis(2-diphenylphosphinoethyl)phenylphosphine trioxide | [bisdppeO$_3$]. |

The oxides of monodentate phosphines, dioxides of bidentate phosphines (except for dppfcO$_2$ and dppcbO$_2$), and trioxides of tridentate phosphines are generally prepared by the oxidation of the corresponding phosphine with aqueous hydrogen peroxide in ethanol, as described in: Ellermann, J.; Schirmacher, D. Chem. Ber. 1967, 100, 2220; Siegl, W. O.; Lapporte, S. J.; Collman, J. P. Inorg. Chem. 1971, 10, 2158; Lindner, E.; Beer, H. Chem. Ber. 1972, 105, 3261. The hydrogen peroxide oxidation is also used to prepare dppcbO$_2$, but in THF at room temperature.

The bis-phosphine monoxides can be synthesized via the selective Pd-catalyzed biphasic anaerobic oxidation of the corresponding bidentate phosphines with 1,2-dibromoethane in the presence of alkali, as described in: Grushin, V. V. J. Am. Chem. Soc. 1999, 121, 5831; U.S. Pat. No. 5,919,984, 1999. This Pd-catalyzed oxidation is also applied to the preparation of dppfcO$_2$.

The monophosphine oxide diphenyl phosphonimide trisphenyl phosphorane [OPNP] is known to form complexes of the formula Ln($\beta$-enolate)$_3$(OPNP)$_1$. It has been found in the present study, that it is possible to form complexes of the formula Ln($\beta$-enolate)$_3$(OPNP)$_2$. OPNP can conveniently be prepared by refluxing bis(triphenylphosphine)iminium chloride in aqueous NaOH.

Bis-phosphine oxide-sulfide Ligands

The bisphosphine oxide-sulfide ligands have Formula III, given above. Examples of suitable bisphosphine oxide-sulfide ligands include, but are not limited to those listed in Table (iv) below. The abbreviation for the ligand is given in brackets.

TABLE (iv)

| (1-diphenylphosphoryl-1-diphenylthiophosphoryl)methane | [dppmOS] |
| (1-diphenylphosphoryl-2-diphenylthiophosphoryl)ethane | [dppeOS] |
| (1-diphenylphosphoryl-3-diphenylthiophosphoryl)propane | [dpppOS] |

These ligands can be prepared by the reaction of the corresponding bisphosphine mono-oxide with elemental sulfur.

Pyridine N-Oxide Ligands

The pyridine N-oxide ligands have Formula IV, Formula V, or Formula VI, shown in FIG. 2. Examples of suitable pyridine N-oxide ligands include, but are not limited to those listed in Table (v) below. The abbreviation for the ligand is given in brackets.

TABLE (v)

| Formula IV | pyridine N-oxide | [pyO]; and |
| | 3-cyanopyridine N-oxide | [CNpyO] |
| Formula V | unsubstituted isoquinoline N-oxide | |
| Formula VI | bipyridine bis(N-oxide) | [bipyO$_2$] |

The nitrogen oxide ligands are generally prepared by oxidation of corresponding pyridines using oxidants such as peroxyacids.

Phosphine oxide-pyridine N-oxide Ligands

The phosphine oxide-pyridine N-oxide ligands have Formula VII shown in FIG. 3. Examples of this type of ligand include but are not limited to those listed in Table (vi) below:

TABLE (vi)

| 2-(diphenylphosphinoyl)-pyridine-1-oxide | [dpOpyO] |
| 2-[(diphenylphosphinoyl)methyl]-pyridine-1-oxide | [dpmOpyO] |

These ligands can be available commercially, or can be made by the oxidation of the corresponding phosphine oxide-pyridine compound as described in: Bodrin, G. V.; Matveeva, A. G.; Terekhova, M. I.; Matrosov, E. I.; Petrov, E. S.; Polikarpov, Yu. M.; Kabachnik, M. I. Izv. Akad. Nauk. SSSR, Ser. Khim. 1991, 912 and McCabe, D. J.; Russell, A. A.; Karthikeyan, S.; Paine, R. T.; Ryan, R. R.; Smith, B. Inorg. Chem. 1987, 26, 1230.

$\beta$-Enolate Ligands

Figure 4:
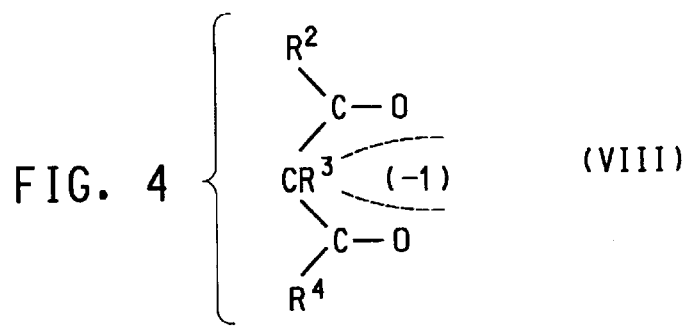
FIG. 4 shows Formula VIII for enolate ligands useful in the invention.

The term "$\beta$-enolate" is a ligand having Formula VIII, shown in FIG. 4, wherein $R^2$, $R^3$, $R^4$ can be alike or different from each other and are selected from hydrogen, halogen, substituted or unsubstituted alkyl, aryl, alkylaryl or heterocyclic groups; or adjacent R groups can be joined to form five- and six-membered rings, which can be substituted, and may be N-, O-, or S-containing heterocyclic rings.

Preferred $R^2$ and $R^4$ groups are selected from H, F, —$C_tH_uF_v$, —$C_6H_5$ which may be substituted with alkyl, aryl, halide, or combinations thereof, —$C_4H_3S$, and —$C_4H_3O$, where t is an integer from 1 to 6, and u and v are integers such that u+v=2t+1. Preferred $R^3$ groups are H, —$CH_2$-aryl, halide, and $C_tH_uF_v$.

Examples of suitable β-enolate ligands include, but are not limited to, those listed in Table (vii) below. The abbreviation for the β-enolate form is given in brackets.

TABLE (vii)

| | |
|---|---|
| 2,4-pentanedionate | [acac] |
| 1,3-diphenyl-1,3-propanedionate | [DI] |
| 2,2,6,6-tetramethyl-3,5-heptanedionate | [TMH] |
| 1-(2-thienyl)4,4,4-trifluoroacetonate | [TTFA] |
| 7,7-dimethyl-1,1,1,2,2,3,3-heptafluoro-4,6-octanedionate | [FOD] |
| 1,1,1,5,5,5-hexafluoro-2,4-pentanedionate | [$F_6$acac] |
| 1,1,1,3,5,5,5-heptafluoro-2,4-pentanedionate | [$F_7$acac] |
| 1-phenyl-3-methyl-4-i-butyryl-5-pyrazolinonate | [PMBP]] |

The β-dicarbonyl compounds are generally available commercially. 1,1,1,3,5,5,5-heptafluoro-2,4-pentanedione, $CF_3C(O)CFHC(O)CF_3$, can be prepared using a two-step synthesis, based on the reaction of perfluoropentene-2 with ammonia, followed by a hydrolysis step as described by M. A. Kurykin, L. S. German, I. L. Knunyants Izv. AN USSR. Ser. Khim. 1980, pp.2817–2829. This compound should be stored and reacted under anyhydrous conditions as it is susceptible to hydrolysis.

Lanthanide Complexes

The lanthanide phosphine oxide and bis-phosphine oxide-sulfide complexes of the invention can be made by the addition of the β-dicarbonyl and phosphine oxide or bis-phosphine oxide-sulfide compounds to a simple lanthanide metal salt, such as the chloride, nitrate, or acetate. One synthetic method is to dissolve an anhydrous lanthanide acetate, the desired β-dicarbonyl and the phosphine oxide in dichloromethane. The product can be precipitated by the addition of hexanes. This is particularly useful for forming complexes with $F_7$acac. The $F_7$acac lanthanide complexes are generally quite stable to air and moisture. Another synthetic route that can be used employs the reaction of a tris(β-enolate)lanthanide complex with phosphine oxide or bis-phosphine oxide-sulfide ligands in dichloromethane. The product can be isolated from solvents such as hexane or acetone/hexane.

Examples of lanthanide complexes with phosphine monoxides having the Formula (IX) above, are given in Table 1 below.

TABLE 1

| Compound | Ln | β-enolate | phosphine oxide | 1 or 2 |
|---|---|---|---|---|
| 1-a | Eu | acac | dppmO | 2 |
| 1-b | Eu | acac | dppeO | 2 |
| 1-c | Eu | acac | dpppO | 2 |
| 1-d | Eu | acac | dppbO | 2 |
| 1-e | Eu | acac | $F_5$tpO | 2 |
| 1-f | Eu | DI | dppmO | 2 |
| 1-g | Eu | DI | dppeO | 2 |
| 1-h | Eu | DI | dpppO | 2 |
| 1-i | Eu | DI | dppbO | 2 |
| 1-j | Eu | DI | $F_5$tpO | 2 |
| 1-k | Eu | TMH | dppmO | 1 |

TABLE 1-continued

| Compound | Ln | β-enolate | phosphine oxide | 1 or 2 |
|---|---|---|---|---|
| 1-l | Eu | TMH | dppeO | 1 |
| 1-m | Eu | TMH | dpppO | 1 |
| 1-n | Eu | TMH | dppbO | 1 |
| 1-o | Eu | TMH | $F_5$tpO | 1 |
| 1-p | Eu | TTFA | dppmO | 2 |
| 1-q | Eu | TTFA | dppeO | 2 |
| 1-r | Eu | TTFA | dpppO | 2 |
| 1-s | Eu | TTFA | dppbO | 2 |
| 1-t | Eu | TTFA | $F_5$tpO | 2 |
| 1-u | Eu | FOD | dppmO | 2 |
| 1-v | Eu | FOD | dppeO | 2 |
| 1-w | Eu | FOD | dpppO | 2 |
| 1-x | Eu | FOD | dppbO | 2 |
| 1-y | Eu | FOD | $F_5$tpO | 2 |
| 1-z | Eu | $F_7$acac | dppmO | 2 |
| 1-aa | Eu | $F_7$acac | dppeO | 2 |
| 1-ab | Eu | $F_7$acac | dpppO | 2 |
| 1-ac | Eu | $F_7$acac | dppbO | 2 |
| 1-ad | Eu | $F_7$acac | $F_5$tpO | 2 |
| 1-ae | Tb | acac | dppmO | 2 |
| 1-af | Tb | acac | dppeO | 2 |
| 1-ag | Tb | acac | dpppO | 2 |
| 1-ah | Tb | acac | dppbO | 2 |
| 1-ai | Tb | acac | $F_5$tpO | 2 |
| 1-aj | Tb | TMH | dppmO | 1 |
| 1-ak | Tb | TMH | dppeO | 1 |
| 1-al | Tb | TMH | dpppO | 1 |
| 1-am | Tb | TMH | dppbO | 1 |
| 1-an | Tb | TMH | $F_5$tpO | 1 |
| 1-ao | Tb | TTFA | dppmO | 2 |
| 1-ap | Tb | TTFA | dppeO | 2 |
| 1-aq | Tb | TTFA | dpppO | 2 |
| 1-ar | Tb | TTFA | dppbO | 2 |
| 1-as | Tb | TTFA | $F_5$tpO | 2 |
| 1-at | Tb | $F_7$acac | dppmO | 2 |
| 1-au | Tb | $F_7$acac | dppeO | 2 |
| 1-av | Tb | $F_7$acac | dpppO | 2 |
| 1-aw | Tb | $F_7$acac | dppbO | 2 |
| 1-ax | Tb | $F_7$acac | $F_5$tpO | 2 |
| 1-ay | Tm | TMH | dppmO | 1 |
| 1-az | Tm | TMH | dppeO | 1 |
| 1-ba | Tm | TMH | dpppO | 1 |
| 1-bb | Tm | TMH | dppbO | 1 |
| 1-bc | Tb | PMBP | $F_5$tpO | 2 |
| 1-bd | Eu | $F_6$acac | dppmO | 2 |
| 1-be | Eu | $F_6$acac | dppeO | 2 |

Examples of lanthanide complexes with bisphosphine dioxides having Formula X above, where there is one Ln(β-enolate)$_3$ unit per phosphine oxide ligand, are given in Table 2 below.

TABLE 2

| Compound | Ln | β-enolate | phosphine oxide |
|---|---|---|---|
| 2-a | Eu | acac | dppmO$_2$ |
| 2-b | Eu | acac | dppeO$_2$ |
| 2-c | Eu | acac | dpppO$_2$ |
| 2-d | Eu | acac | dppFeO$_2$ |
| 2-e | Eu | acac | $F_5$dppeO$_2$ |
| 2-f | Eu | DI | dppmO$_2$ |
| 2-g | Eu | DI | dppeO$_2$ |
| 2-h | Eu | DI | dpppO$_2$ |
| 2-i | Eu | DI | dppFeO$_2$ |
| 2-j | Eu | DI | $F_5$dppeO$_2$ |
| 2-k | Eu | TMH | dppmO$_2$ |
| 2-l | Eu | TMH | dppeO$_2$ |
| 2-m | Eu | TMH | dpppO$_2$ |
| 2-n | Eu | TMH | dppfcO$_2$ |
| 2-o | Eu | TMH | $F_5$dppeO$_2$ |
| 2-p | Eu | TTFA | dppmO$_2$ |
| 2-q | Eu | TTFA | dppeO$_2$ |
| 2-r | Eu | TTFA | dpppO$_2$ |

TABLE 2-continued

| Compound | Ln | β-enolate | phosphine oxide |
|---|---|---|---|
| 2-s | Eu | TTFA | dppFeO$_2$ |
| 2-t | Eu | TTFA | F$_5$dppeO$_2$ |
| 2-u | Eu | FOD | dppmO$_2$ |
| 2-v | Eu | FOD | dppeO$_2$ |
| 2-w | Eu | FOD | dpppO$_2$ |
| 2-x | Eu | FOD | dppFeO$_2$ |
| 2-y | Eu | FOD | F$_5$dppeO$_2$ |
| 2-z | Eu | F$_7$acac | dppmO$_2$ |
| 2-aa | Eu | F$_7$acac | dppeO$_2$ |
| 2-ab | Eu | F$_7$acac | dpppO$_2$ |
| 2-ac | Eu | F$_7$acac | dppFeO$_2$ |
| 2-ad | Eu | F$_7$acac | F$_5$dppeO$_2$ |
| 2-ae | Tb | acac | dppmO$_2$ |
| 2-af | Tb | acac | dppeO$_2$ |
| 2-ag | Tb | acac | dpppO$_2$ |
| 2-ah | Tb | acac | dppFeO$_2$ |
| 2-ai | Tb | acac | F$_5$dppeO$_2$ |
| 2-aj | Tb | TMH | dppmO$_2$ |
| 2-ak | Tb | TMH | dppeO$_2$ |
| 2-al | Tb | TMH | dpppO$_2$ |
| 2-am | Tb | TMH | dppFeO$_2$ |
| 2-an | Tb | TMH | F$_5$dppeO$_2$ |
| 2-ao | Tb | TTFA | dppmO$_2$ |
| 2-ap | Tb | TTFA | dppeO$_2$ |
| 2-aq | Tb | TTFA | dpppO$_2$ |
| 2-ar | Tb | TTFA | dppFeO$_2$ |
| 2-as | Tb | TTFA | F$_5$dppeO$_2$ |
| 2-at | Tb | F$_7$acac | dppmO$_2$ |
| 2-au | Tb | F$_7$acac | dppeO$_2$ |
| 2-av | Tb | F$_7$acac | dpppO$_2$ |
| 2-aw | Tb | F$_7$acac | dppFeO$_2$ |
| 2-ax | Tb | F$_7$acac | FsdppeO$_2$ |
| 2-ay | Tm | TMH | dppmO$_2$ |
| 2-az | Tm | TMH | dppeO$_2$ |
| 2-ba | Tm | TMH | dpppO$_2$ |
| 2-bb | Tm | TMH | dppFeO$_2$ |
| 2-bc | Tm | TMH | F$_5$dppeO$_2$ |
| 2-bd | Tb | PMBP | dpppO$_2$ |

Complexes of the lanthanide metals with pyridine N-oxides, having Formula XIII above, can be made in CH$_2$Cl$_2$ solvent following a reaction of dry metal acetate with excess of the corresponding β-dicarbonyl compound, followed by addition of the N-oxide compound. Novel complexes with pyridine N-oxides are isolated in 60–90% yield in analytically pure form and characterized by nuclear magnetic resonance (NMR) spectroscopy.

According to data from single crystal X-ray diffraction, the isolated complexes exist in dimeric form with two metals bound through the oxygens of three pyridine N-oxides. Examples of lanthanide complexes with pyridine N-oxides are given in Table 3 below. The complex has Formula XIII, shown above.

TABLE 3

| Compound | Ln | β-enolate | N-oxide Formula | α | δ | Y |
|---|---|---|---|---|---|---|
| 3-a | Eu | F$_6$acac | IV | 0 | — | — |
| 3-b | Tb | F$_6$acac | IV | 0 | — | — |
| 3-c | Tm | F$_6$acac | IV | 0 | — | — |
| 3-d | Eu | F$_6$acac | IV | 1 | — | 4-CN |
| 3-e | Tb | F$_6$acac | IV | 1 | — | 4-CN |
| 3-f | Eu | FOD | IV | 0 | — | — |
| 3-g | Eu | F$_7$acac | IV | 0 | — | — |
| 3-h | Eu | F$_6$acac | V | 0 | 0 | — |

Electronic Device

Figure 7:
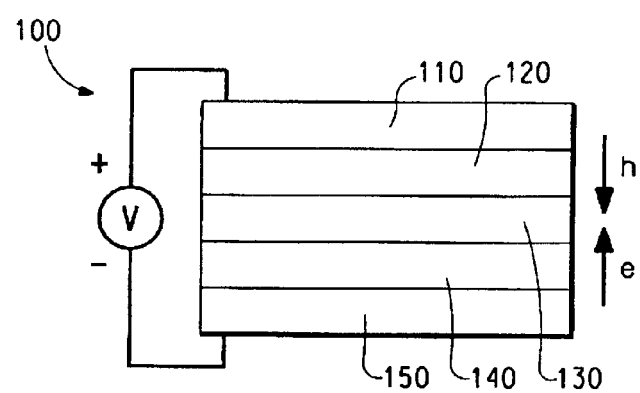
FIG. 7 is a schematic diagram of a light-emitting device (LED).

The present invention also relates to an electronic device comprising at least one photoactive layer positioned between two electrical contact layers, wherein the at least one photoactive layer of the device includes the lanthanide complex of the invention. As shown in FIG. 7, a typical device 100 has an anode layer 110 and a cathode layer 150 and electroactive layers 120, 130 and optionally 140 between the anode 110 and cathode 150. Adjacent to the anode 110 is a hole injection/transport layer 120. Adjacent to the cathode 150 is an optional layer 140 comprising an electron transport material. Between the hole injection/transport layer 120 and the cathode (or optional electron transport layer) is the photoactive layer 130.

Depending upon the application of the device 100, the photoactive layer 130 can be a light-emitting layer that is activated by an applied voltage (such as in a light-emitting diode or light-emitting electrochemical cell), a layer of material that responds to radiant energy and generates a signal with or without an applied bias voltage (such as in a photodetector). Examples of photodetectors include photoconductive cells, photoresistors, photoswitches, phototransistors, and phototubes, and photovoltaic cells, as these terms are describe in Markus, John, *Electronics and Nucleonics Dictionary*, 470 and 476 (McGraw-Hill, Inc. 1966).

The lanthanide complexes of the invention are useful in the photoactive layer 130 of the device. For some lanthanide complexes (such as Tb and Eu), the luminescence spectrum is due to f-f transitions within the metal. Thus, while the intensity of emission can be influenced by the nature of the ligands attached to the lanthanide metal, the wavelength remains relatively constant for all complexes of the same metal. The europium complexes typically have a sharp red emission; the terbium complexes have a sharp green emission. For some lanthanides (such as Tm), the luminescence observed is not due to atomic transitions of the metal. Rather, it is due to either the ligands or the metal-ligand interaction. Under such conditions, the luminescence band can be broad and the wavelength can be sensitive to the ligand used.

While the complexes can be used alone in the light-emitting layer, their emission generally is not strong. It has been found that emission can be greatly improved by combining the lanthanide complexes with materials which facilitate charge transport. The materials can be hole transport materials, electron transport materials or other light-emitting materials which have good transport properties. If the lanthanide complex does not have good hole transport properties, a hole transport material can be co-deposited. Conversely, an electron transport material can be co-deposited if the lanthanide complex does not have good electron transport properties. Some materials can transport both electrons and holes and are more flexible to use.

To achieve a high efficiency LED, the HOMO (highest occupied molecular orbital) of the hole transport material should align with the work function of the anode, the LUMO (lowest un-occupied molecular orbital) of the electron transport material should align with the work function of the cathode. Chemical compatibility and sublimation temp of the materials are also important considerations in selecting the electron and hole transport materials.

Figure 5:
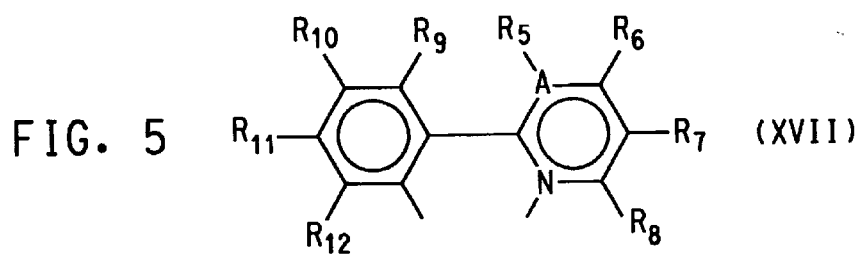
FIG. 5 shows Formula XVII for a phenylpyridine ligand.

It is preferred to use hole transport materials such as N,N'-diphenyl-N,N'-bis(3-methylphenyl)-[1,1'-biphenyl]-4,4'-diamine (TPD) and bis[4-(N,N-diethylamino)-2-methylphenyl](4-methylphenyl)methane (MPMP); electron and hole transporting material such as 4,4'-N,N'-dicarbazole biphenyl (BCP); or light-emitting materials with good electron and hole transport properties, such as chelated oxinoid compounds, such as tris(8-hydroxyquinolato)aluminum (Alq$_3$), and cyclometalated iridium complexes with 2-phenylpyridines and derivatives. The iridium complexes have been described in copending application Ser. No. 60/215362. They can be generally described as compound having Formula XVI below:

$$IrL^a{}_bL^c{}_xL'{}_yL''{}_z \qquad (XVI)$$

where:
x=0 or 1, y=0, 1 or 2, and z=0 or 1, with the proviso that:
x=0 or y+z=0 and
when y=2 then z=0;
L'=a bidentate ligand or a monodentate ligand, and is not a phenylpyridine, phenylpyrimidine, or phenylquinoline; with the proviso that:
when L' is a monodentate ligand, y+z=2, and
when L' is a bidentate ligand, z=0;
L''=a monodentate ligand, and is not a phenylpyridine, and phenylpyrimidine, or phenylquinoline; and
$L^a$, $L^b$ and $L^c$ are alike or different from each other and each of $L^a$, $L^b$ and $L^c$ has Formula XVII, shown in FIG. 5
wherein:
adjacent pairs of $R^5$–$R^8$ and $R^9$–$R^{12}$ can be joined to form a five- or six-membered ring,
at least one of $R^5$–$R^{12}$ is selected from F, —$C_sF_{2s+1}$, —$OC_sF_{2s+1}$, and —$OCF_2Y$, where s=1–6 and Y=H, Cl, or Br, and
A=C or N, provided that when A=N, there is no $R^5$.

Preferred iridium compounds include those where $L^a=L^b=L^c$, and either (i) $R^7$ is $CF_3$, $R^{11}$ is F, and all other R are H; or (ii) $R^{10}$ is $CF_3$ and all other R are H. The iridium complexes above are generally prepared from the appropriate substituted 2-phenylpyridine, phenylpyrimidine, or phenylquinoline. The substituted 2-phenylpyridines, phenylpyrimidines, and phenylquinolines are prepared, in good to excellent yield, using the Suzuki coupling of the substituted 2-chloropyridine, 2-chloropyrimidine or 2-chloroquinoline with arylboronic acid as described in O. Lohse, P.Thevenin, E. Waldvogel *Synlett*, 1999, 45–48. The iridium complex can then be prepared by reacting an excess of the 2-phenylpyridine, phenylpyrimidine, or phenylquinoline, without a solvent, with iridium trichloride hydrate and 3 equivalents of silver trifluoracetate.

When the lanthanide complex is co-deposited with additional charge transport material to form the photoactive layer, the lanthanide complex is generally present in an amount of about up to 85% by volume (15% by volume for the charge transport material) based on the total volume of the emitting layer. Under such conditions the charge transport material is responsible for carrying the electrons and/or holes to the lanthanide. The concentration of the charge transport material has to be above the percolation threshold of approximately 15 volume %, such that a conducting pathway can be established. When the density of the material is close to one, 15 wt % is acceptable as long as the percolation threshold is reached.

In some cases the lanthanide complexes may be present in more than one isomeric form, or mixtures of different complexes may be present. It will be understood that in the above discussion of devices, the term "the lanthanide compound" is intended to encompass mixtures of compounds and/or isomers.

The device generally also includes a support (not shown) which can be adjacent to the anode or the cathode. Most frequently, the support is adjacent the anode. The support can be flexible or rigid, organic or inorganic. Generally, glass or flexible organic films are used as a support. The anode 110 is an electrode that is particularly efficient for injecting or collecting positive charge carriers. The anode is preferably made of materials containing a metal, mixed metal, alloy, metal oxide or mixed-metal oxide. Suitable metals include the Group 11 metals, the metals in Groups 4, 5, and 6, and the Group 8–10 transition metals. If the anode is to be light-transmitting, mixed-metal oxides of Groups 12, 13 and 14 metals, such as indium-tin-oxide, are generally used. The anode 110 may also comprise an organic material such as polyaniline as described in "Flexible light-emitting diodes made from soluble conducting polymer," *Nature* vol. 357, pp 477–479 (11 Jun. 1992).

The anode layer 110 is usually applied by a physical vapor deposition process or spin-cast process. The term "physical vapor deposition" refers to various deposition approaches carried out in vacuo. Thus, for example, physical vapor deposition includes all forms of sputtering, including ion beam sputtering, as well as all forms of vapor deposition such as e-beam evaporation and resistance evaporation. A specific form of physical vapor deposition which is useful is rf magnetron sputtering.

There is generally a hole transport layer 120 adjacent the anode. Examples of hole transport materials for layer 120 have been summarized for example, in Kirk-Othmer Encyclopedia of Chemical Technology, Fourth Edition, Vol. 18, p. 837–860, 1996, by Y. Wang. Both hole transporting molecules and polymers can be used. Commonly used hole transporting molecules, in addition to TPD and MPMP mentioned above, are: 1,1-bis[(di-4-tolylamino)phenyl] cyclohexane (TAPC), N,N'-bis(4-methylphenyl)-N,N'-bis (4-ethylphenyl)-[1,1'-(3,3'-dimethyl)biphenyl]-4,4'-diamine (ETPD), tetrakis-(3-methylphenyl)-N,N,N', N'-2,5-phenylenediamine (PDA), a-phenyl-4-N,N-diphenylaminostyrene (TPS), p-(diethylamino) benzaldehyde diphenylhydrazone (DEH), triphenylamine (TPA), 1-phenyl-3-[p-(diethylamino)styryl]-5-[p-(diethylamino)phenyl]pyrazoline (PPR or DEASP), 1,2-trans-bis(9H-carbazol-9-yl)cyclobutane (DCZB), N,N,N', N'-tetrakis(4-methylphenyl)-(1,1'-biphenyl)-4,4'-diamine (TTB), and porphyrinic compounds, such as copper phthalocyanine. Commonly used hole transporting polymers are polyvinylcarbazole, (phenylmethyl)polysilane, poly(3,4-ethylendioxythiophene) (PEDOT), and polyaniline. It is also possible to obtain hole transporting polymers by doping hole transporting molecules such as those mentioned above into polymers such as polystyrene and polycarbonate.

Optional layer 140 can function both to facilitate electron transport, and also serve as a buffer layer or confinement layer to prevent quenching reactions at layer interfaces. Preferably, this layer promotes electron mobility and reduces quenching reactions. Examples of electron transport materials for optional layer 140 include metal chelated oxinoid compounds, such as tris(8-hydroxyquinolato) aluminum ($Alq_3$); phenanthroline-based compounds, such as 2,9-dimethyl-4,7-diphenyl-1,10-phenanthroline (DDPA) or 4,7-diphenyl-1,10-phenanthroline (DPA), and azole compounds such as 2-(4-biphenylyl)-5-(4-t-butylphenyl)-1,3,4-oxadiazole (PBD) and 3-(4-biphenylyl)-4-phenyl-5-(4-t-butylphenyl)-1,2,4-triazole (TAZ).

The cathode 150 is an electrode that is particularly efficient for injecting or collecting electrons or negative charge carriers. The cathode can be any metal or nonmetal having a lower work function than the first electrical contact layer (in this case, an anode). Materials for the second electrical contact layer can be selected from alkali metals of Group 1 (e.g., Li, Cs), the Group 2 (alkaline earth) metals, the Group 12 metals, the lanthanides, and the actinides.

Materials such as aluminum, indium, calcium, barium, samarium and magnesium, as well as combinations, can be used.

It is known to have other layers in organic electronic devices. For example, there can be a layer (not shown) between the hole transport layer 120 and the photoactive layer 130 to facilitate positive charge transport and/or band-gap matching of the layers, or to function as a protective layer. Similarly, there can be additional layers (not shown) between the photoactive layer 130 and the cathode layer 150 to facilitate negative charge transport and/or band-gap matching between the layers, or to function as a protective layer. Layers that are known in the art can be used. In addition, any of the above-described layers can be made of two or more layers. Alternatively, some or all of inorganic anode layer 110, the hole transport layer 120, the photoactive layer 130, and cathode layer 150, may be surface treated to increase charge carrier transport efficiency. The choice of materials for each of the component layers is preferably determined by balancing the goals of providing a device with high device efficiency.

It is understood that each functional layer may be made up of more than one layer.

The device can be prepared by sequentially vapor depositing the individual layers on a suitable substrate. Substrates such as glass and polymeric films can be used. Conventional vapor deposition techniques can be used, such as thermal evaporation, chemical vapor deposition, and the like. Alternatively, the organic layers can be coated from solutions or dispersions in suitable solvents, using any conventional coating technique. In general, the different layers will have the following range of thicknesses: anode 110, 500–5000 Å, preferably 1000–2000 Å; hole transport layer 120, 50–2500 Å, preferably 200–2000 Å; light-emitting layer 130, 10–1000 Å, preferably 100–800 Å; optional electron transport layer 140, 50–1000 Å, preferably 200–800 Å; cathode 150, 200–10,000 Å, preferably 300–5000 Å. The location of the electron-hole recombination zone in the device, and thus the emission spectrum of the device, is affected by the relative thickness of each layer. For examples, when an emitter, such as $Alq_3$ is used as the electron transport layer, the electron-hole recombination zone can be in the $Alq_3$ layer. The emission would then be that of $Alq_3$, and not the desired sharp lanthanide emission. Thus the thickness of the electron-transport layer must be chosen so that the electron-hole recombination zone is in the light-emitting layer. The desired ratio of layer thicknesses will depend on the exact nature of the materials used.

It is understood that the efficiency of the devices of the invention made with lanthanide compounds, can be further improved by optimizing the other layers in the device. For example, more efficient cathodes such as Ca, Ba or LiF can be used. Shaped substrates and novel hole transport materials that result in a reduction in operating voltage or increase quantum efficiency are also applicable. Additional layers can also be added to tailor the energy levels of the various layers and facilitate electroluminescence.

EXAMPLES

The following examples illustrate certain features and advantages of the present invention. They are intended to be illustrative of the invention, but not limiting. All percentages are by weight, unless otherwise indicated.

In Examples 5, 13, 14, and 16–22, photoluminescence of the lanthanide complexes was determined qualitatively by placing the solid samples under UV light and observing the color of emission.

Example 1

Synthesis of PMBP: 7.5 g 1-phenyl-3-methyl-pyrazolinone was dissolved by warming in 45 mL p-dioxane. While stirring rapidly, 6 g calcium hydroxide was added to the refluxing solution and then immediately thereafter 4.4 mL i-butyrylchloride was also added. After an initial white precipitate formed, the solution was stirred and refluxed for 30 mins during which time the initial solid dissolved and a second white precipitate formed. The solution was cooled and then poured into 100 mL 2M HCl whereupon it becomes dark red and red crystals form on standing for 48 hrs at room temperature. A mixture of red and white needle-like crystals was collected by filtration and washed well with distilled water. Recrystallization from 50:50 methanol:water (wherein the water is pH=4 with HCl) yields 73% fluffy white crystals of the desired product were collected washed with water and vacuum dried.

$Tb(PMBP)_3$: 1.7 g terbium nitrate tris-dimethylsulfoxide was dissolved into 20 mL methanol and 2.4 g of the ligand PMBP from above was added in 20 mL toluene. The cloudy solution was stirred while 2 mL triethylamine was added. After 15 mins the solution was evaporated to dryness and the oily solid was first washed well with water and then vacuum dried. The oily white solid was recrystallized from hot toluene:octane 1:1 as a white powder. This complex exhibited intense green photoluminescent (365 nm ex).

$Tb(PMBP)_3(F_5tpO)_2$: 1 g of the tris-(1-phenyl-3-methyl-4-i-butyryl-5-pyrozolone)terbium, $Tb(PMBP)_3$, was dissolved in 10 mL methylene chloride and then mixed with 0.7 g perfluorotriphenylphosphine oxide also dissolved in 10 mL methylene chloride. The mixture was stirred for 30 mins then evaporated to dryness and the white residue was recrystallized from toluene.

Example 2

This example is illustrative of a typical synthesis of Ln (β-dienolate)$_3$ (bisphosphine dioxide), where β-dienolate is acac, DI, FOD, TMH.

$Eu(FOD)_3(dpppO_2)$. To a dichloromethane (5 mL) solution of $Eu(FOD)_3$ (0.875 g, 0.844 mmol) was added a $dpppO_2$ (0.375 g, 0.844 mmol) dissolved in dichloromethane (10 mL). The resulting mixture was stirred for 48 h. The solvent was allowed to evaporate and the resulting white powder was washed with hexanes, then dried under vacuum. The powder was isolated in 62% yield (0.771 g). $^{31}P\{1H\}$ NMR ($CD_2Cl_2$, 202 MHz) δ is −48.9.

Example 3

OPNP. To a solution of NaOH (10 g) in water (30 mL) was added bis(triphenylphosphine)iminium chloride (3.00 g), and the mixture was stirred under reflux for 2 hours. After addition of water (50 mL) the thick organic oil was separated from the aqueous phase and wahsed with water. The oily solid was dissolved in dichloromethane (50 mL), the resulting solution was filtered through silica gel, reduced in volume to ca. 10 mL, treated with hexanes (200 mL), and left overnight. The precipitate was dissolved in dichloromethane (5 mL), and then treated first with ether (10 mL) and after 30 min with hexanes (100 mL). After 1.5 hours white crystals of OPNP were separated, washed with hexanes, and dried under vacuum. The yield of spectroscopically pure OPNP was 1.40 g (56%). $^{31}P$ NMR ($CH_3OH$), δ: 17.8 (d, 1P, J=3.7 Hz), 15.1 (d., 1P, J=3.7 Hz).

$Eu(FOD)_3(OPNP)_2$. To a dichloromethane (5 mL) solution of $Eu(FOD)_3$ (0.627 g, 0.651 mmol) was added a OPNP (0.599 g, 1.255 mmol) dissolved in dichloromethane (10 mL). The resulting mixture was stirred for 48 h. The solvent was allowed to evaporate and the resulting yellow solid was washed with hexanes, then dried under vacuum. The solid was isolated in 92% yield (1.15 g).

Example 4

This example is illustrative of a typical synthesis of Ln (β-dienolate)$_3$ (bisphosphine dioxide), where β-dienolate= acac, DI, TMH, FOD.

Eu(FOD)$_3$(dppeO$_2$). To a dichloromethane (5 mL) solution of Eu(FOD)$_3$ (0.884 g, 0.852 mmol) was added a dppeO$_2$ (0.366 g, 0.852 mmol) dissolved in dichloromethane (10 mL). The resulting mixture was stirred for 48 h. The solvent was allowed to evaporate and the resulting white powder was washed with hexanes, then dried under vacuum. The powder was isolated in 62% yield (0.771 g). $^{31}$P{1H} NMR (CD$_2$Cl$_2$, 202 MHz) δ is −49.9.

Example 5

(F$_7$acac)$_3$Eu(OPNP)$_2$. 1,1,1,3,5,5,5-heptafluoro-2,4-pentanedione (F7-acetylacetone) was prepared according to the procedure in M. A. Kurykin, L. S. German, Knunaynts, I. L. *Izv. Akad. Nauk. SSSR, Ser. Khim.* 1980, 2827., and O. E. Petrova, M. A. Kurykin, D. V. Gorlov *Izv. Akad. Nauk. SSSR, Ser. Khim.* 1999, 1710. In a glove-box, the F7-acetylacetone (315 mg) was added to a stirred mixture of dry Eu(OAc)$_3$ (127 mg), OPNP (374 mg), and dichloromethane (1 mL). After a few minutes all solids dissolved. Hexane (6 mL) was added the clear yellow solution turned cloudy. After the solution cleared, additional 15 mL of hexane was added and the mixture was kept at 0° C. for 2 hours. Well-shaped crystals were separated, recrystallized from dichloromethane-hexanes, and dried under vacuum. The yield was 510 mg (74%). $^1$H NMR (CD$_2$Cl$_2$), δ: 6.0 (br. s., Ph), 6.8 (br. m., Ph), 7.1 (m, Ph); 7.7 (m, Ph). $^{19}$F NMR (CD$_2$Cl$_2$), δ: −74.5 (d, 7F, J=17.5 Hz), −184.7 (heptet, 1F, J=17.5 Hz). $^{31}$P NMR (CD$_2$Cl$_2$), δ: 15.1 (d, 1P, J=8.5 Hz), −128.8 (d, 1P, J=8.5 Hz). Anal.Calcd for C$_{75}$H$_{50}$EuF$_{21}$N$_2$O$_8$P$_4$: C, 50.6; H, 2.8; N, 1.6. Found: C, 51.3; H, 2.9; N, 1.6. This complex exhibited red photoluminescence.

Example 6

Eu(FOD)$_3$(F5tpO)$_2$ To a dichloromethane (5 mL) solution of Eu(FOD)$_3$ (0.608 g, 0.586 mmol) was added a F5tpO (0.642 g, 1.172 mmol) dissolved in dichloromethane (10 mL). The resulting mixture was stirred for 48 h. The solvent was allowed to evaporate and the resulting white powder was washed with hexanes, then dried under vacuum. The powder was isolated in 78% yield (1.036 g). $^{31}$P{1H} NMR (CD$_2$Cl$_2$, 202 MHz) δ −49.3.

Example 7

Tb(PMBP)$_3$(dpppO$_2$). 0.11 g of the tris-(1-phenyl-3-methyl-4-i-butyryl-5-pyrozolone)terbium, Tb (PMBP)$_3$, was dissolved in 5 mL methylene chloride and then mixed with 0.054 g bisdiphenylphosphinopropane dioxide also dissolved in 5 mL methylene chloride. The mixture was stirred for 30 mins then evaporated to dryness and the white residue was recrystallized from toluene.

Example 8

Eu(DI)$_3$(dppbO)$_2$. To a dichloromethane (2 mL) solution of Eu(DI)$_3$ (0.161 g, 0.195 mmol) was added a dppbO (0.173 g, 0.391 mmol) dissolved in dichloromethane (2 mL). The resulting mixture was stirred for 48 h. The solvent was allowed to evaporate and the resulting yellow solid was washed with hexanes, then dried under vacuum. A yellow powder was isolated in 87% yield (0.291 g). $^{31}$P{1H} NMR (CD$_2$Cl$_2$, 202 MHz) δ −15.32. Anal.Calcd for C$_{71}$H$_{69}$EuO$_8$P$_4$:C, 71.1; H, 5.26; P, 7.26. Found: C, 69.50; H, 4.47; N, 6.60.

Example 9

This example is illustrative of a typical synthesis of Ln(TMH)$_3$(monophosphine oxide).

Eu(TMH)$_3$(dpppO). To a dichloromethane (2 mL) solution of the Eu(TMH)$_3$ was added dpppO (0.092 g, 0.124 mmol) dissolved in dichloromethane (2 mL) and then stirred for 48 h. The solvent was allowed to evaporate, and the resulting white solid was washed with hexanes, then dried under vacuum. A white powder was isolated in 36% yield (0.089 g).

Example 10

This example is illustrative of a typical synthesis of Ln (TTFA)$_3$ (monophosphine oxide)$_2$.

Eu(TTFA)$_3$(F$_5$tpO)$_2$. To a solution of 1-(2-thenoyl) 4,4,4-trifluoroacetate (0.162 g, 0.729 mmol) in dichloromethane (2 mL), triethylamine would be added (0.101 mL, 0.729 mmol) followed by Eu(NO$_3$)$_3$.xH$_2$O (0.108 g, 0.242 mmol) in methanol (2 mL) and F$_5$tpO (0.135 g, 0.486 mmol) in dichloromethane (2 mL). The reaction would be stirred for 48 h followed by evaporation of solvent. The resulting cream powder would be recrystallised from acetone/hexanes with a yield of 50–60%.

Example 11

This example is illustrative of a typical synthesis of Ln(TTFA)$_3$ (bisphosphine dioxide).

Eu(TTFA)$_3$(dpppO$_2$). To a solution of 1-(2-thienyl)4,4,4-trifluoroacetate (0.176 g, 0.792 mmol) in dichloromethane (2 mL), triethylamine was added (0.111 mL, 0.792 mmol) followed by Eu(NO$_3$)$_3$.xH$_2$O (0.118 g, 0.265 mmol) in methanol (2 mL) and dpppO$_2$ (0.118 g, 0.265 mmol) in dichloromethane (2 mL). The reaction was stirred for 48 h. The solvent was allowed to evaporate and the resulting solid was recrystallized from CH$_2$Cl$_2$/hexanes. A fluffy yellow solid was isolated in 93% yield (0.310 g). $^{31}$P{1H} NMR (CD$_2$Cl$_2$, 202 MHz) δ is −47.77 (s).

Example 12

[Eu(F$_7$acac)$_3$(OPPh$_3$)$_2$]. In a glove-box, the F7-acetylacetone made as in Example 5 (540 mg) was added to a stirred mixture of dry Eu(OAc)$_3$ (224 mg), Ph$_3$PO (439 mg), and dichloromethane (3 mL). After a few minutes all solids dissolved. Hexane (15 mL) was added to the clear yellow solution and the mixture was left at room temperature overnight. Large yellow crystals of the title complex were separated, washed with hexane, and dried under vacuum. The yield was 630 mg (67%). $^1$H NMR (CD$_2$Cl$_2$), δ: 7.9 (br. m., Ph). $^{19}$F NMR (CD$_2$Cl$_2$), δ: −76.9 (7F), −184.9 (1F). $^{31}$P NMR (CD$_2$Cl$_2$), δ: −91.0 (s). Anal.Calcd for C$_{51}$H$_{30}$EuF$_{21}$O$_8$P$_2$: C, 44.3; H, 2.2. Found: C, 44.2; H, 2.3. The structure of the complex was confirmed by single-crystal X-ray diffraction. This complex exhibited red photoluminescence.

Example 13

[Eu(F$_6$acac)$_3$(dppeO)$_2$]. To a stirring mixture of Eu(OAc)$_3$ (130 mg), dppeO (330 mg), and dichloromethane (ca. 1 mL) was added 1,1,1,5,5,5-hexafluoro-2,4-pentanedione (260 mg). All solids dissolved after a few minutes. Hexane (20 mL) was added and the solution was kept at 0° C. for 1 hour, then left at room temperature overnight. The white needle-shaped crystals were separated, washed with hexanes, and dried under vacuum. The yield was 555 mg (88%). $^1$H NMR (CD$_2$Cl$_2$), δ: 3.2 (br. s.), 4.6 (br. s.), 5.8 (br. s.), 7.5 (br. m, Ph); 8.0 (br. m, Ph). $^{19}$F NMR (CD$_2$Cl$_2$), δ: −79.7 (s). $^-$P NMR (CD$_2$Cl$_2$), δ: −9.9 (d, 1P, J=47.5 Hz), −83.2 (d., 1P, J=47.5 Hz). Anal.Calcd for C$_{67}$H$_{51}$EuF$_{18}$O$_8$P$_4$: C, 50.2; H, 3.2 Found: C, 50.1; H, 3.2. This complex exhibited red photoluminescence.

Example 14

[Eu(F$_6$acac)$_3$(dppmO)$_2$]. A mixture of Eu(OAc)$_3$ (200 mg), dppmO (502 mg), hexafluoro-2,4-pentanedione (0.44 g), and dichloromethane (4 mL) was stirred for 10 min. The solution was filtered to remove a small amount of insolubles. The clear filtrate was reduced in volume to ca. 1 mL and treated with hexanes (2 mL). After 10 min the white crystalline solid was separated, washed with hexanes, and dried under vacuum. The yield was 0.793 g (83%). Anal. Calcd. for C$_{65}$H$_{47}$O$_8$F18EuP$_4$,: C, 49.6; H, 3.0. Found: C, 49.4; H, 2.8. $^1$H NMR (CD$_2$Cl$_2$, 20 C): 4.4 (br d, J=15.5 Hz, 4H, CH2), 5.8 (br s, 3H, OCCHCO), 7.3 (br m, 24H, 3,4-C6H5), 8.0 (br m, 16H, 2-C6H5). $^{31}$P NMR (CD$_2$Cl$_2$, 20 C); −25.2 (br s, 2P, Ph$_2$P), −78.2 (br s, 2P, Ph$_2$PO). $^{19}$F NMR (CD$_2$Cl$_2$, 20 C): −79.9 (s).

Examples 15–21

These examples illustrate the synthesis of polyfluoroacetylacetonato-pyridine oxide complexes of Eu and Tb.

Example 15

[(F$_6$acac)$_3$Eu]$_2$(pyO)$_3$. Inside a glove-box, 1,1,1,5,5,5-hexafluoro-2,4-pentanedione (360 mg) was added to a stirred mixture of dry Eu(OAc)$_3$ (170 mg) and dichloromethane (4 mL). After a few minutes, all solids dissolved and 150 mg of pyridinium N-oxide was added. White precipitate started to form immediately. After 2 h solid was washed with hexane (15 mL), filtered and dried under vacuum. The material was found to be a binuclear complex of Eu, where two europium atoms (each coordinated to 3 molecules of hexafluoroacetylacetonato ligands) were bridged through oxygen atoms of 3 molecules of pyridinium N-oxide. The yield was 550 mg (57%). $^1$H NMR (acetone-d$_6$), δ: 5.88 (br. s.), 6.65 (br. s), 8.61 (br, s) ratio 1:1:2. $^{19}$F NMR (acetone-d$_6$), δ: −79.12(s). Anal.Calcd for C$_{45}$H$_{21}$Eu$_2$F$_{36}$N$_3$O$_{15}$: C, 29.49; H, 1.14, N, 2.29 Found: C, 29.32; H, 1.03, N, 2.22. The structure of the complex was confirmed by single-crystal X-ray diffraction. The complex exhibited red photoluminescence.

Example 16

[(F$_6$acac)$_3$Tb]$_2$(pyO)$_3$. Inside a glove-box, 1,1,1,5,5,5-hexafluoro-2,4-pentanedione (660 mg) was added to a stirred mixture of dry Tb(OAc)$_3$ (340 mg) and dichloromethane (4 mL). After a few minutes all solids dissolved and 190 mg of pyridinium N-oxide was added. White precipitate started to form immediately. After 2 h solid was washed with hexane (15 mL), filtered and dried under vacuum. The material was found to be a binuclear complex of Tb, where two terbium atoms (each coordinated to 3 molecules of hexafluoroacetylacetonato ligands) were bridged through oxygen atoms of 3 molecules of pyridinium N-oxide. The yield was 990 mg (54%). $^1$H NMR (acetone-d$_6$), δ: 1.90(br. s.). $^{19}$F NMR (acetone-d$_6$), δ: 65.63(br. s.), −86.48(s). Anal.Calcd for C$_{45}$H$_{21}$Tb$_2$F$_{36}$N$_3$O$_{15}$: C, 29.26; H, 1.14, N, 2.27 Found: C, 29.45; H, 1.36, N, 2.36.

The compound exhibited green photoluminescence.

Example 17

[(F$_7$acac)$_3$Eu]$_2$(pyO)$_3$. Inside a glove-box, 1,1,1,3,5,5,5-heptafluoro-2,4-pentanedione (720 mg) was added to a stirred mixture of dry Eu(OAc)$_3$ (320 mg) and dichloromethane (4 mL). After a few minutes all solids dissolved and 190 mg of pyridinium N-oxide was added. White precipitate started to form immediately. After 2 h solid was washed with hexane (15 mL), filtered and dried under vacuum. The material was found to be a binuclear complex of Eu, where two europium atoms (each coordinated to 3 molecules of hexafluoroacetylacetonato ligands) were bridged through oxygen atoms of 3 molecules of pyridinium N-oxide. The yield was 990 mg (54%), yellow needles. $^1$H NMR (acetone-d$_6$), δ: 3.20(br. s.), 6.8 (br s), 10.0 (br s). $^{19}$F NMR (acetone-d$_6$), δ: −76.40 (6F, br. s.), −184.23 (s). Anal. Calcd for C$_{45}$H$_{15}$Eu$_2$F$_{42}$N$_3$O$_{15}$: C, 27.84; H, 0.77, N, 2.17 Found: C, 27.76; H, 0.95, N, 2.24. Compound exhibited no photoluminescence.

Example 18

[(F$_6$acac)$_3$Eu]$_2$(CNpyO)$_3$. Inside a glove-box, 1,1,1,5,5,5-hexafluoro-2,4-pentanedione (640 mg) was added to a stirred mixture of dry Eu(OAc)$_3$ (340 mg) and dichloromethane (4 mL). After a few minutes all solids dissolved and 150 mg of pyridinium N-oxide was added. White precipitate started to form immediately. After 2 h solid was washed with hexane (15 mL), filtered and dried under vacuum. The material was found to be a binuclear complex of Eu, where two europium atoms (each coordinated to 3 molecules of hexafluoroacetylacetonato ligands) were bridged through oxygen atoms of 3 molecules of pyridinium N-oxide. The yield was 850 mg (45%). $^1$H NMR (acetone-d$_6$), δ: 3.1 (br. s.), 3.6 (br s), 7.60 (br s), 8.60 (br s) in ratio 1:2:2:1. $^{19}$F NMR (acetone-d$_6$), δ: −81.14(s). Anal. Calcd for C$_{48}$H$_{18}$Eu$_2$F$_{36}$N$_6$O$_{15}$: C, 30.24; H, 0.95, N, 4.41 Found: C, 30.67; H, 1.00, N, 4.77. The complex exhibited red photoluminescence.

Example 19

[(F$_6$acac)$_3$Eu]$_2$(iso-Quinoline-oxide)$_3$. Inside a glove-box, 1,1,1,5,5,5-hexafluoro-2,4-pentanedione (640 mg) was added to a stirred mixture of dry Eu(OAc)$_3$ (340 mg) and dichloromethane (5 mL). After a few minutes all solids dissolved and 210 mg of isoquinoline-N-oxide was added. After 2 h hexane (15 mL) was added and next morning crystals were filtered and dried under vacuum. The material was found to be a binuclear complex of Eu, where two europium atoms (each coordinated to 3 molecules of hexafluoroacetylacetonato ligands) were bridged through oxygen atoms of 3 molecules of isoquinoline-N-oxide. The yield was 1300 mg mg (66%). $^1$H NMR (acetone-d$_6$), δ: 3.0 (br. s.), 6.5 (br. s.), 7.2 (br. s.), 7.8 (br. s.), 8.0 (br. s.), 10.0 (br. s.), in ratio 4:2:2:1:2:2 . $^{19}$F NMR (acetone-d$_6$), δ: −79.44(s). Anal. Calcd for C$_{57}$H$_{27}$Eu$_2$F$_{36}$N$_3$O$_{15}$: C, 34.55; H, 1.37; N, 2.12. Found: C, 34.44; H, 1.22, N, 2.12. The structure of the complex was confirmed by single-crystal X-ray diffraction. The complex exhibited red photoluminescence.

Example 20

[(FOD)$_3$Eu]$_2$(pyO)$_3$. Inside a glove-box, 2,2-dimethyl-6,6,7,7,8,8,8-heptafluoro-3,5-octanedione (FOD) (890 mg)

was added to a stirred mixture of dry Eu(OAc)$_3$ (330 mg) and dichloromethane (4 mL) followed by 180 mg of pyridinium N-oxide. After 2 h 15 ml of hexane was added and reaction mixture was kept in refrigerator overnight. Next morning solid was washed with hexane (15 mL), filtered and dried under vacuum. The yield was 1560 mg (68%). $^1$H NMR (acetone-d$_6$), 0.3 (br s), 7.40 (br s), 8.30 (br s), 10.1 (br s), integrated as 28:2:2:1:2.

$^{19}$F NMR (acetone-d$_6$), δ: −82.57 (3F), −126.50(2F), −129.63 (2F). Anal. Calcd for C$_{75}$H$_{75}$Eu$_2$F$_{42}$N$_3$O$_{15}$: C, 38.17; H, 3.20; N, 1.78. Found: C,37.26; H, 3.00; N, 1.40. The complex exhibited red photoluminescence.

Example 21

[(F$_6$acac)$_3$Tb]$_2$(CNpyO)$_3$. Inside a glove-box, 1,1,1,5,5,5-hexafluoro-2,4-pentanedione (620 mg) was added to a stirred mixture of dry Tb(OAc)$_3$ (340 mg) and dichloromethane (5 mL). After a few minutes all solids dissolved and 180 mg of p-CN-pyridinium-N-oxide was added. White precipitate started to form immediately. After 6 h solid was washed with hexane (15 mL), filtered and dried under vacuum. The material was found to be a binuclear complex of Eu, where two terbium atoms (each coordinated to 3 molecules of hexafluoroacetylacetonato ligands) were bridged through oxygen atoms of 3 molecules of p-CN-pyridinium N-oxide. The yield was 1200 mg (63%). $^1$H NMR (acetone-d$_6$), δ: 7.0 (br. s.). $^{19}$F NMR (acetone-d$_6$), δ: −56.99 (br.s), −62.36 (br.s), −65.03(s), integrated as 4.5:1:1. Calcd for C$_{48}$H$_{18}$Tb$_2$F$_{36}$N$_6$O$_{15}$ C, 30.02; H, 1.02, N, 4.38. Found: C, 28.90; H, 1.02, N, 5.16. The complex exhibited green photoluminescence.

Example 22

This example illustrates the preparation of iridium complexes which can be used as a charge transport material.
(a) Preparation of 2-phenylpyridine Ligands The general procedure used was described in O. Lohse, P. Thevenin, E. Waldvogel Synlett, 1999, 45–48. In a typical experiment, a mixture of 200 ml of degassed water, 20 g of potassium carbonate, 150 ml of 1,2-dimethoxyethane, 0.5 g of Pd(PPh$_3$)$_4$, 0.05 mol of a substituted 2-chloropyridine and 0.05 mol of a substituted phenylboronic acid was refluxed (80–90° C.) for 16–30 h. The resulting reaction mixture was diluted with 300 ml of water and extracted with CH$_2$Cl$_2$ (2×100 ml). The combined organic layers were dried over MgSO$_4$, and the solvent removed by vacuum. The liquid products were purified by fractional vacuum distillation. The solid materials were recrystallized from hexane. The typical purity of isolated materials was >98%. The starting materials, yields, melting and boiling points of two 2-phenylpyridines were:

a1: 2-(4-fluorophenyl)-5-trifluoromethylpyridine
yield 94%. mp=38–40° C.; b.p. 65–67° C./0.07 mm Hg $^1$H NMR=7.08(2H), 7.62(1H), 7.90(3H), 8.80(1H), $^{19}$F NMR=−62.75 (3F,s) −111.49 (m) Analysis (calculated): C, 60.39 (59.75), H,3.38 (2.90), N, 5.5 (5.51)

a2: 2-(3-trifluoromethylphenyl)pyridine
yield 72%, bp=64–65° C./64–65/0.026 mm Hg; $^1$H NMR=7.20(1H), 7.65(4H), 8.1(1H), 8.20(1H), 8.65(1H) $^{19}$F NMR=−63.05 (3F,s)

(b) Preparation of Iridium Complexes, IrL$_3$

A mixture of IrCl$_3$.nH$_2$O (54% Ir; 508 mg), 2-(4-fluorophenyl)-5-trifluoromethylpyridine, compound (a1) (2.20 g), AgOCOCF$_3$ (1.01 g), and water (1 mL) was vigorously stirred under a flow of N$_2$ as the temperature was slowly (30 min) brought up to 185° C. (oil bath). After 2 hours at 185–190° C. the mixture solidified. The mixture was cooled down to room temperature. The solids were extracted with dichloromethane until the extracts decolorized. The combined dichloromethane solutions were filtered through a short silica column and evaporated. After methanol (50 mL) was added to the residue the flask was kept at −10° C. overnight. The yellow precipitate of the tris-cyclometalated complex, compound 23-a having Formula XVIII shown in FIG. 6, was separated, washed with methanol, and dried under vacuum. Yield: 1.07 g (82%). X-Ray quality crystals of the complex were obtained by slowly cooling its warm solution in 1,2-dichloroethane.

Figure 6:
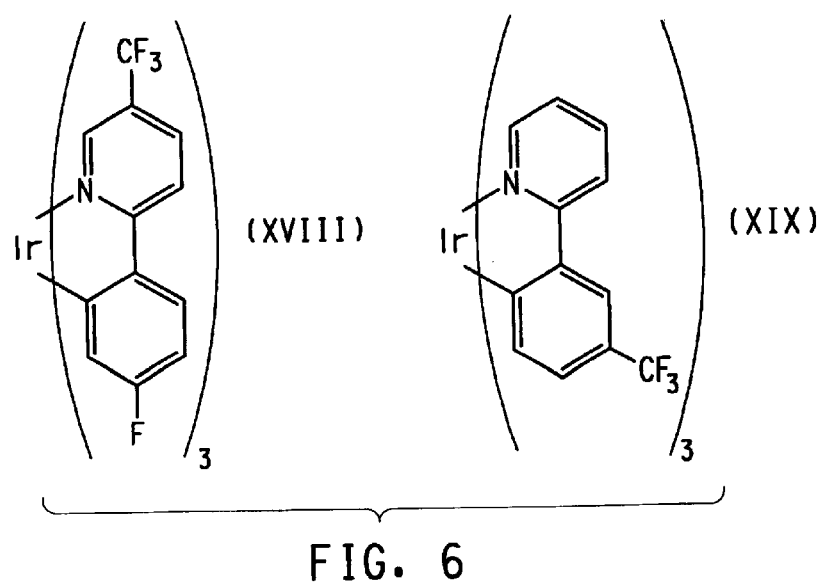
FIG. 6 shows Formula XVIII and Formula XIX for cyclometalated iridium complexes.

Compound 23-b, having Formula XIX shown in FIG. 6, was prepared using the same procedure as above using 2-(3-trifluoromethylphenyl)pyridine.

Example 23 dppcbO$_2$: To a solution of 1,2-bis(diphenylphosphino)-o-carborane (0.59 g) in dichloromethane (15 mL) was added 30% hydrogen peroxide (0.3 mL) and the mixture was vigorously stirred at room temperature. After 1 hour, analysis of the organic phase by $^{31}$P NMR indicated 95% conversion. One more 0.3 mL portion of 30% hydrogen peroxide was added and the mixture was stirred for one more hour to reach 100% conversion ($^{31}$P NMR). The organic phase was filtered through cotton wool and evaporated. The white crystalline residue was dried under vacuum to give 1,2-o-C$_2$B$_{10}$H$_{10}$(P(O)Ph$_2$)$_2$×H$_2$O quantitatively (0.65 g). $^1$H NMR (CD$_2$Cl$_2$): 7.0–7.2 ppm (m, 3H, m,p-C$_6$H$_4$); 8.2 ppm (m, 2H, o-C$_6$H$_4$). $^{31}$P NMR (CD$_2$Cl$_2$): 22.7 ppm (s).

Complexes of the type Ln(β-enolate)$_3$(dppcbO$_2$) can be prepared following the procedure decribed in Example 2.

Examples 24–25

These examples illustrate the synthesis of bimetallic complexes having Formula XV.

Example 24

{Eu(TMH)$_3$dppmO}$_2$PdCl$_2$: A CH$_2$Cl$_2$ (5 mL) solution of PdCl$_2$ (dppmO)$_2$ was added to a CH$_2$Cl$_2$ (5 mL) of Eu(TMH)$_3$. The resulting solution was stirred at room temperature overnight. The volatiles were evaporated to yield a yellow crystalline solid. The product can be recrystallized from hot CH$_2$Cl$_2$. This compound exhibited red photoluminescence.

Example 25

[(acac-F$_6$)$_3$Eu(μ-dppeO)$_2$PdCl$_2$]$_n$: To a solution of [(acac-F$_6$)$_3$Eu(dppeO)$_2$] (160 mg) in dichloromethane (3 mL) was added a solution of [Pd(PhCN)$_2$Cl$_2$] (38 mg) in dichloromethane (2 mL). The brown solution of the Pd complex turned yellow immediately. After the solvent was removed under vacuum the residual oily solid was re-precipitated from dichloromethane (1 mL) with hexane (15 mL) upon trituration. Further trituration with 4 mL of hexane produced a yellow powder. The yield was 164 mg (92%). Anal.Calcd for (C$_{67}$H$_{51}$Cl$_2$EuF$_{18}$O$_8$P$_4$Pd)$_n$: C, 45.2; H, 2.9. Found: C, 45.8; H, 3.0. This polymer (oligomer) exhibited red photoluminescence.

Example 26

This example illustrates the formation of OLEDs using the lanthanide complexes of the invention.

Thin film OLED devices including a hole transport layer (HT layer), electroluminescent layer (EL layer) and at least one electron transport layer (ET layer) were fabricated by the thermal evaporation technique. An Edward Auto 306 evaporator with oil diffusion pump was used. The base vacuum for all of the thin film deposition was in the range of $10^{-6}$ torr. The deposition chamber was capable of depositing five different films without the need to break up the vacuum.

An indium tin oxide (ITO) coated glass substrate was used, having an ITO layer of about 1000–2000 Å. The substrate was first patterned by etching away the unwanted ITO area with 1N HCl solution, to form a first electrode pattern. Polyimide tape was used as the mask. The patterned ITO substrates were then cleaned ultrasonically in aqueous detergent solution. The substrates were then rinsed with distilled water, followed by isopropanol, and then degreased in toluene vapor for ~3 hours. Alternatively, patterned ITO from Thin Film Devices, Inc was used. These ITO's are based on Corning 1737 glass coated with 1400 Å ITO coating, with sheet resistance of 30 ohms/square and 80% light transmission.

The cleaned, patterned ITO substrate was then loaded into the vacuum chamber and the chamber was pumped down to $10^{-6}$ torr. The substrate was then further cleaned using an oxygen plasma for about 5–10 minutes. After cleaning, multiple layers of thin films were then deposited sequentially onto the substrate by thermal evaporation. Finally, patterned metal electrodes of Al were deposited through a mask. The thickness of the film was measured during deposition using a quartz crystal monitor (Sycon STC-200). All film thickness reported in the Examples are nominal, calculated assuming the density of the material deposited to be one. The completed OLED device was then taken out of the vacuum chamber and characterized immediately without encapsulation.

A summary of the device layers and thicknesses is given in Table 5. In all cases the anode was ITO as discussed above, and the cathode was Al having a thickness in the range of 700–760 Å. In some of the samples, a two-component electroluminescent (EL) layer was used which contained both the lanthanides and charge-transport materials. In that case, a mixture of the two components, in the ratio indicated, was used as the starting material and evaporated as described above.

TABLE 5

| Sample | HT layer Thickness, Å | EL layer thickness, Å | ET layer thickness, Å |
|---|---|---|---|
| 1 | MPMP 523 | Example 1 639 | Alq$_3$ 416 |
| 2 | MPMP 570 | Example 2 + TPD (1:1) 423 | DPA, 107 + Alq$_3$, 414 |
| 3 | MPMP 525 | Example 3 + TPD (1:1) 406 | DPA, 119 + Alq$_3$, 311 |
| 4 | MPMP 524 | Example 4 + TPD (1:1) 414 | DDPA, 109 + Alq$_3$, 306 |
| 5 | MPMP 507 | Example 5 + TPD (1:1) 406 | DDPA 407 |
| 6 | MPMP 518 | Example 1 + TPD (1:1) 410 | DDPA 405 |
| 7 | MPMP 553 | Example 6 + MPMP (1:1) 451 | DPA, 108 + Alq$_3$, 307 |
| 8 | MPMP 524 | Example 7 412 | DPA, 410 |

Figure 8:
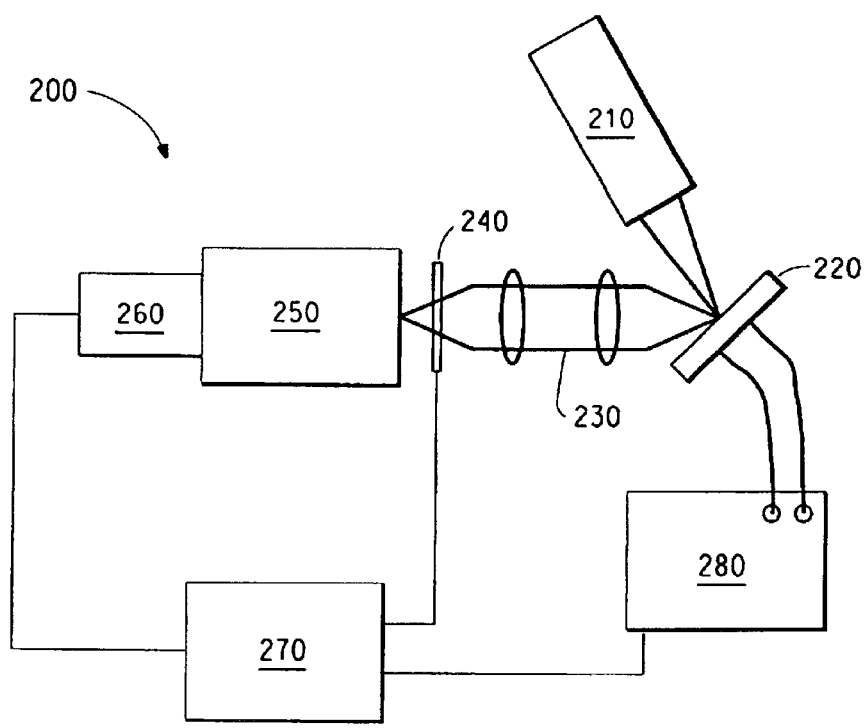
FIG. 8 is a schematic diagram of an LED testing apparatus.

Alq$_3$ = tris(8-hydroxyquinolato) aluminum
DPA = 4,7-diphenyl-1,10-phenanthroline
DDPA = 2,9-dimethyl-4,7-diphenyl-1,10-phenanthroline
ET = electron transport
HT = hole transport
MPMP = bis[4-(N,N-diethylamino)-2-methylphenyl](4-methylphenyl) methane The OLED samples were characterized by measuring their (1) current-voltage (I-V) curves, (2) electroluminescence radiance versus voltage, and (3) electroluminescence spectra versus voltage. The apparatus used, 200, is shown in FIG. 8. The I-V curves of an OLED sample, 220, were measured with a Keithley Source-Measurement Unit Model 237, 280. The electroluminescence radiance (in the unit of Cd/m$^2$) vs. voltage was measured with a Minolta LS-110 luminescence meter, 210, while the voltage was scanned using the Keithley SMU. The electroluminescence spectrum was obtained by collecting light using a pair of lenses, 230, through an electronic shutter, 240, dispersed through a spectrograph, 250, and then measured with a diode array detector, 260. All three measurements were performed at the same time and controlled by a computer, 270. The efficiency of the device at certain voltage is determined by dividing the electroluminescence radiance of the LED by the current density needed to run the device. The unit is in Cd/A.

The results are given in Table 6 below.

TABLE 6

Electroluminescent Properties of Lanthanide Complexes

| Sample | Peak Radiance, cd/m$^2$ | Peak efficiency, cd/A | Approximate Peak Wavelengths, nm |
|---|---|---|---|
| 1 | 30 | 0.43 | 550 |
| 2 | 2 | 0.11 | 617 |
| 3 | 4.5 | 0.18 | 617 |
| 4 | 5 | 0.08 | 617 |
| 5 | 5.5 | 0.015 | 617 |
| 6 | 7 | 0.021 | 550 |
| 7 | 0.5 | 0.01 | 617 |
| 8 | 6 | 0.5 | 550 |

What is claimed is:

1. A lanthanide compound having one of Formulae IX-A and IX-B below:

Ln(β-enolate)$_3$(monophosphine oxide)$_1$     (IX-A)

Ln(β-enolate)$_3$(monophosphine oxide)$_2$     (IX-B)

where:
in Formulae (IX-A) and (IX-B):
monophosphine oxide has Formula I:

O$_2$P(O)—Z     (I)

such that:
Q is the same or different at each occurrence and is selected from C$_6$H$_n$F$_{5-n}$, and C$_m$(H+F)$_{2m+1}$,
m is an integer from 1 to 12, and
n is 0 or an integer from 1 to 5, and
Z is selected from Q and pyridiyl, with the provision that when Z is Q, there is at least one F substituent on at least one Q group.

2. The compound of claim 1 wherein the Ln is selected from Eu, Tb and Tm.

3. The compound of claim 1 wherein the monophosphine oxide is selected from tris(pentafluorophenyl)phosphine oxide, 2-(diphenylphosphinoyl)-pyridine.

4. The compound of claim 1 wherein the β-enolate is selected from 2,4-pentanedionate; 1,3-diphenyl-1,3-propanedionate; 2,2,6,6-tetramethyl-3,5-heptanedionate; 1-(2-thienyl)4,4,4-trifluoroacetate; 7,7-dimethyl-1,1,1,2,2,3,3-heptafluoro-4,6-octanedionate; 1,1,1,5,5,5-hexafluoro-2,4-pentanedionate; 1,1,1,3,5,5,5-heptafluoro-2,4-pentanedionate; and 1-phenyl-3-methyl-4-i-butyryl-5-pyrazolinonate.

5. An electronic device comprising a photoactive layer, wherein the photoactive layer comprises the lanthanide compound of Claim 1.

6. The device of claim 5 wherein the lanthanide compound is present in an amount of up to about 85% by volume based on the total volume of the photoactive layer.

7. The device of claim 5 wherein the photoactive layer further comprises a charge transport material.

8. The device of claim 7 wherein the charge transport material is a hole transport material and is selected from N,N'-diphenyl-N,N'-bis(3-methylphenyl)-[1,1'-biphenyl]-4,4'-diamine; bis[4-(N,N-diethylamino)-2-methylphenyl](4-methylphenyl)methane; and combinations thereof.

9. The device of claim 7 wherein the charge transport material is an electron transporting material and is selected from 4,4'-N,N'-dicarbazole biphenyl; chelated oxinoid compounds of aluminum; cyclometalated iridium complexes with 2-phenylpyridines; and combinations thereof.

10. The device of claim 5, further comprising a hole transport layer comprising a hole transport material selected from N,N'-diphenyl-N,N'-bis(3-methylphenyl)-[1,1'-biphenyl]-4,4'-diamine; 1,1-bis[(di-4-tolylamino)phenyl]cylohexane; N,N'-bis(4-methylphenyl)-N,N'-bis(4-ethylphenyl)-[1,1'-(3,3'-dimethyl)biphenyl]-4,4'-diamine; tetrakis-(3-methylphenyl)-N,N,N',N'-2,5-phenylenediamine; α-phenyl-4-N,N-diphenylaminostyrene; p-(diethylamino)benzaldehyde diphenylhydrazone; triphenylamine; bis[4-(N,N-diethylamino)-2-methylphenyl](4-methylpheny methane; 1-phenyl-3-[p-(diethylamino) styryl]-5-[p-(diethylamino)phenyl]pyrazoline;1,2-trans-bis(9H-carbazol-9-yl)cyclobutane; N,N,N',N'-tetrakis(4-methylphenyl)-(1,1'-biphenyl)-4,4'-diamine; porphyrinic compounds; and combinations thereof.

11. The device of claim 5, further comprising electron transport layer comprising an electron transport material selected from tris(8-hydroxyquinolato)aluminum; 2,9-dimethyl-4,7-diphenyl-1,10-phenanthroline; 4,7-diphenyl-1,10-phenanthroline; 2-(4-biphenylyl)-5-(4-t-butylphenyl)-1,3,4-oxadiazole; 3-(4-biphenylyl)-4-phenyl-5-(4-t-butylphenyl)-1,2,4-triazole; and combination thereof.

12. A lanthanide compound having one of Formulae IX-A and IX-B below:

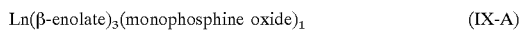
$$Ln(\beta\text{-enolate})_3(\text{monophosphine oxide})_1 \quad (IX\text{-}A)$$

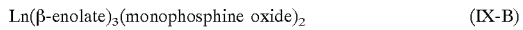
$$Ln(\beta\text{-enolate})_3(\text{monophosphine oxide})_2 \quad (IX\text{-}B)$$

and selected from Compound 1-a to Compound 1-b below:

TABLE 1

| Compound | Ln | β-enolate | phosphine oxide | 1 or 2 |
|---|---|---|---|---|
| 1-a | Eu | acac | dppmO | 2 |
| 1-b | Eu | acac | dppeO | 2 |
| 1-c | Eu | acac | dpppO | 2 |
| 1-d | Eu | acac | dppbO | 2 |
| 1-e | Eu | acac | F$_5$tpO | 2 |
| 1-f | Eu | DI | dppmO | 2 |
| 1-g | Eu | DI | dppeO | 2 |
| 1-h | Eu | DI | dpppO | 2 |
| 1-i | Eu | DI | dppbO | 2 |
| 1-j | Eu | DI | F$_5$tpO | 2 |
| 1-k | Eu | TMH | dppmO | 1 |
| 1-l | Eu | TMH | dppeO | 1 |
| 1-m | Eu | TMH | dpppO | 1 |
| 1-n | Eu | TMH | dppbO | 1 |
| 1-o | Eu | TMH | F$_5$tpO | 1 |
| 1-p | Eu | TTFA | dppmO | 2 |

TABLE 1-continued

| Compound | Ln | β-enolate | phosphine oxide | 1 or 2 |
|---|---|---|---|---|
| 1-q | Eu | TTFA | dppeO | 2 |
| 1-r | Eu | TTFA | dpppO | 2 |
| 1-s | Eu | TTFA | dppbO | 2 |
| 1-t | Eu | TTFA | F$_5$tpO | 2 |
| 1-u | Eu | FOD | dppmO | 2 |
| 1-v | Eu | FOD | dppeO | 2 |
| 1-w | Eu | FOD | dpppO | 2 |
| 1-x | Eu | FOD | dppbO | 2 |
| 1-y | Eu | FOD | F$_5$tpO | 2 |
| 1-z | Eu | F$_7$acac | dppmO | 2 |
| 1-aa | Eu | F$_7$acac | dppeO | 2 |
| 1-ab | Eu | F$_7$acac | dpppO | 2 |
| 1-ac | Eu | F$_7$acac | dppbO | 2 |
| 1-ad | Eu | F$_7$acac | F$_5$tpO | 2 |
| 1-ae | Tb | acac | dppmO | 2 |
| 1-af | Tb | acac | dppeO | 2 |
| 1-ag | Tb | acac | dpppO | 2 |
| 1-ah | Tb | acac | dppbO | 2 |
| 1-ai | Tb | acac | F$_5$tpO | 2 |
| 1-aj | Tb | TMH | dppmO | 1 |
| 1-ak | Tb | TMH | dppeO | 1 |
| 1-al | Tb | TMH | dpppO | 1 |
| 1-am | Tb | TMH | dppbO | 1 |
| 1-an | Tb | TMH | F$_5$tpO | 1 |
| 1-ao | Tb | TTFA | dppmO | 2 |
| 1-ap | Tb | TTFA | dppeO | 2 |
| 1-aq | Tb | TTFA | dpppO | 2 |
| 1-ar | Tb | TTFA | dppbO | 2 |
| 1-as | Tb | TTFA | F$_5$tpO | 2 |
| 1-at | Tb | F$_7$acac | dppmO | 2 |
| 1-au | Tb | F$_7$acac | dppeO | 2 |
| 1-av | Tb | F$_7$acac | dpppO | 2 |
| 1-aw | Tb | F$_7$acac | dppbO | 2 |
| 1-ax | Tb | F$_7$acac | F$_5$tpO | 2 |
| 1-ay | Tm | TMH | dppmO | 1 |
| 1-az | Tm | TMH | dppeO | 1 |
| 1-ba | Tm | TMH | dpppO | 1 |
| 1-bb | Tm | TMH | dppbO | 1 |
| 1-bc | Tb | PMBP | F$_5$tpO | 2 |
| 1-bd | Eu | F$_6$acac | dppmO | 2 |
| 1-be | Eu | F$_6$acac | dppeO | 2 | wherein:

acac is 2,4-pentanedionate,

DI is 1,3-diphenyl-1,3-propanedionate,

TMH is 2,2,6,6-tetramethyl-3,5-heptanedionate,

TTFA is 1-(2-thienyl)4,4,4-trifluoroacetonate,

FOD is 7,7-dimethyl-1,1,1,2,2,3,3-heptafluoro-4,6-octanedionate,

F$_6$acac is 1,1,1,5,5,5-hexafluoro-2,4-pentanedionate,

F$_7$acac is 1,1,1,3,5,5,5-heptafluoro-2,4-pentanedionate,

PMBP is 1-phenyl-3-methyl-4-i-butyryl-5-pyrazolinonate, dppmO is (diphenylphosphinomethyl)diphenylphosphine oxide, dppeO is (2-diphenylphosphinoethyl)diphenylphosphine oxide, dpppO is (3-diphenylphosphinoethyl)diphenylphosphine oxide, dppbO is (4-diphenylphosphinoethyl)diphenylphosphine oxide, and F$_5$tpO is tris(pentafluorophenyl)phosphine oxide.

* * * * *